(12) United States Patent
Baldassano et al.

(10) Patent No.: US 10,245,431 B2
(45) Date of Patent: Apr. 2, 2019

(54) REAL-TIME SEIZURE PREDICTION INFORMED BY HIDDEN MARKOV MODEL EVENT STATES

(71) Applicants: The Trustees of the University of Pennsylvania, Philadelphia, PA (US); University of Washington, Seattle, WA (US)

(72) Inventors: Steven N. Baldassano, Philadelphia, PA (US); Brian Litt, Bala Cynwyd, PA (US); Drausin Wulsin, New York, NY (US); Emily Fox, Seattle, WA (US)

(73) Assignees: The Trustees of the University of Pennsylvania, Philadelphia, PA (US); University of Washington, Seattle, WA (US)

( * ) Notice: Subject to any disclaimer, the term of this patent is extended or adjusted under 35 U.S.C. 154(b) by 140 days.

(21) Appl. No.: 15/333,360

(22) Filed: Oct. 25, 2016

(65) Prior Publication Data
US 2017/0113045 A1 Apr. 27, 2017

Related U.S. Application Data
(60) Provisional application No. 62/246,350, filed on Oct. 26, 2015.

(51) Int. Cl.
| | |
|---|---|
| *A61N 1/36* | (2006.01) |
| *A61B 5/0476* | (2006.01) |
| *A61B 5/00* | (2006.01) |
| *G06F 19/00* | (2018.01) |
| *G06N 7/00* | (2006.01) |

(Continued)

(52) U.S. Cl.
CPC ........ *A61N 1/36064* (2013.01); *A61B 5/0476* (2013.01); *A61B 5/4094* (2013.01); *A61B 5/4836* (2013.01); *A61B 5/7267* (2013.01); *A61B 5/7275* (2013.01); *A61N 1/0551* (2013.01); *A61N 1/36139* (2013.01);
(Continued)

(58) Field of Classification Search
CPC .............. A61N 1/36064; A61B 5/0476; A61B 5/4094; G06F 19/345; G06N 7/005
See application file for complete search history.

(56) References Cited

PUBLICATIONS

Wulsin, "Bayesian Nonparametric Modeling of Epileptic Events, A Dissertation in Bioengineering," 2013 (184 pages).
(Continued)

*Primary Examiner* — William Levicky
(74) *Attorney, Agent, or Firm* — Baker & Hostetler LLP

(57) ABSTRACT

Provided is an implantable medical device for predicting and treating electrical disturbances in tissue. The medical device includes an implantable telemetry unit (ITU), and an implantable leads assembly including a first and a second electrode implanted in the tissue. A processor of the ITU is configured to perform training by receiving electrical signals input to the electrode circuit, parsing the electrical signals into dynamic event states using Bayesian Non-Parametric Markov Switching, and modeling each event state as a multi-dimensional probability distribution. The processor of the ITU is further configured to perform analysis of the electrical signals and therapy to the tissue by applying other electrical signals to the multi-dimensional distribution to predict future electrical disturbances in the tissue, and controlling the electrode circuit to apply an electrical therapy signal to the first and second electrodes to mitigate effects of the future electrical disturbances in the tissue.

14 Claims, 16 Drawing Sheets

(51) Int. Cl.
*A61N 1/05* (2006.01)
*A61N 1/372* (2006.01)
*G16H 50/20* (2018.01)

(52) U.S. Cl.
CPC .......... *A61N 1/37211* (2013.01); *G06F 19/00* (2013.01); *G06N 7/005* (2013.01); *G16H 50/20* (2018.01)

(56) References Cited

PUBLICATIONS

Wulsin et al., "Modeling the Complex Dynamics and Changing Correlations of Epileptic Events," Artificial Intelligence Journal, Jul. 29, 2014, pp. 1-43.

REAL-TIME SEIZURE PREDICTION INFORMED BY HIDDEN MARKOV MODEL EVENT STATES

CROSS REFERENCE TO RELATED APPLICATIONS

This application claims benefit of priority to U.S. Provisional Application No. 62/246,350, filed Oct. 26, 2015, the contents of such application being incorporated by reference herein.

STATEMENT REGARDING FEDERALLY SPONSORED RESEARCH

This invention was made with government support under grant/contract numbers P20 NS080181 and U01-NS-073557-01A1 awarded by National Institutes of Health and FA9550-12-1-0406; FA9550-12-1-0453 awarded by the Air Force Office of Scientific Research. The government has certain rights in the invention.

FIELD

This application relates, in general, to a system and a method for seizure prediction. More specifically, the system and method use a Bayesian nonparametric Markov switching process to parse intracranial electroencephalogram (iEEG) data into distinct dynamic event states. Each event state is modeled as a multi-dimensional Gaussian distribution to allow for predictive state assignment. By detecting event states highly specific for seizure onset, based on the Gaussian distribution, the method identifies regions of real-time iEEG data associated with the transition to seizure activity, thereby predicting future seizures.

BACKGROUND

Epilepsy affects over 60 million individuals worldwide, with one quarter of patients having disease refractory to standard therapies including medication and surgery. Automated seizure prediction algorithms have been studied for decades to improve the diagnosis and treatment of epilepsy. More recently, these algorithms have been applied to closed-loop implantable devices designed to detect pre-seizure events and electrically stimulate the brain to abort epileptic activity.

Conventional systems use real-time iEEG data as input to an algorithm to predict onset of epileptic activity and trigger targeted electrical stimulation to arrest potential seizures. However, these conventional systems are often limited by the efficacy of the prediction algorithms. The algorithms used in these conventional devices are typically dependent on extracting and analyzing specific "features" of the iEEG signal, such as amplitude, line length, and area under the curve. These conventional systems have been hampered by high false positive rates, causing unnecessary stimulation to the brain and increased frequency of repeat surgery to replace spent batteries.

SUMMARY

To meet this and other needs, and in view of its purposes, the described system includes an implantable medical device for predicting and treating electrical disturbances in tissue. The medical device includes an implantable telemetry unit (ITU), and an implantable leads assembly including a first and a second electrode implanted in the tissue. A processor of the ITU is configured to perform training by receiving electrical signals input to the electrode circuit, parsing the electrical signals into dynamic event states using Bayesian Non-Parametric Markov Switching, and modeling each event state as a multi-dimensional probability distribution. The processor of the ITU is further configured to perform analysis of the electrical signals and therapy to the tissue by applying other electrical signals to the multi-dimensional distribution to predict future electrical disturbances in the tissue, and controlling the electrode circuit to apply an electrical therapy signal to the first and second electrodes to mitigate effects of the future electrical disturbances in the tissue.

It is understood that the foregoing general description and the following detailed description is exemplary, but not restrictive.

DETAILED DESCRIPTION

Figure 1:
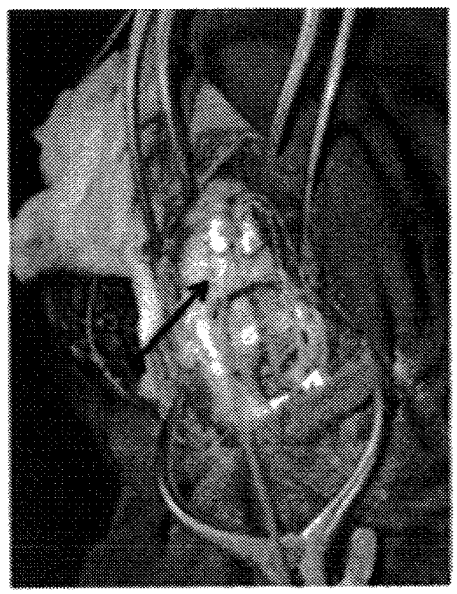
FIG. 1 is a diagram and photograph of an electrode implantation location in a canine neocortex, according to an example embodiment.
Figure 1:
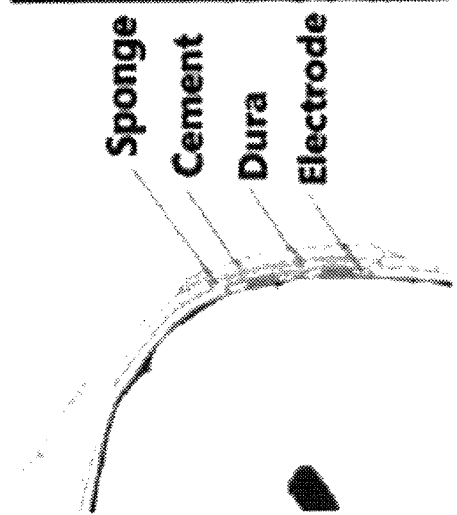

In general, the seizure prediction model described herein is applicable for predicting seizures in human brains. These predictions may be utilized to provide therapy (via electrical stimulation) to the human brain prior to seizure onset in order to prevent or mitigate the effects of the seizure. Although the system and method described herein is applicable to human brains, experimentation described below was performed on seizure prone Dogs during animal testing.

In addition to being applicable to humans and other animals, the system and method described herein is also not limited to seizure prediction. The system and method described herein may be used for predicting other electrical disturbances in brains due to various neurological disorders (e.g. Parkinson's disease, Tremors, Tourette's syndrome, sleep disorders, migraines, etc.), or for predicting electrical disturbances in other parts of the body (e.g. heart arrhythmias, etc.).

As described below, the example embodiments provide a system and a method for use in a robust seizure prediction model. A Bayesian nonparametric Markov switching process is implemented to parse intracranial EEG (iEEG) data into distinct dynamic event states. The parsed states are associated with the pre-seizure events. Each event state is then modeled as a multidimensional Gaussian distribution to allow for predictive state assignment.

By detecting event states highly specific for seizure onset zones, the method identifies precise regions of iEEG data associated with the transition to seizure activity, thereby reducing false positive predictions associated with interictal bursts. Through animal experimentation, the seizure prediction algorithm was evaluated using a total of 391 days of continuous iEEG data containing 55 seizures recorded from 2 dogs with naturally occurring, multifocal epilepsy. A feature-based seizure predictor modeled after the NeuroPace RNS System was developed as a control. The seizure prediction method demonstrated an improvement in false negative rate (0/55 seizures missed vs 2/55 seizures missed) as well as reduced false positive rate (0.0012/hour vs 0.058/hr). All seizures were predicted an average of 12.1±6.9 seconds before the onset of unequivocal epileptic activity (UEO). This algorithm represents a computationally inexpensive, individualized, real-time prediction method suitable for implantable antiepileptic devices that may considerably reduce false positive rate relative to current industry standards.

In order to successfully and reliably avert epileptic activity, it would be beneficial for the prediction algorithm to predict seizure onset with sufficient latency prior to clinical symptoms to provide an opportunity for intervention. Thus, a system is desirably highly sensitive. However, these systems have been hampered by high false positive rates, causing unnecessary stimulation and increased frequency of repeat surgery to replace spent batteries.

One potential source of false positive predictions by feature-based methods is the occurrence of sub-clinical epileptiform "bursts," also known in the literature by terms such as brief ictal rhythmic discharges (B(I)RDs), and others. These events represent an abnormal EEG finding without obvious clinical manifestations, and often occur with greater frequency than seizures. Although the underlying pathology of these discharges remains uncertain, burst activity is associated with epilepsy, neonatal seizures, and brain trauma, and indicates poorer prognosis in long-term clinical outcomes.

The dynamics of burst events closely mimic those of the seizure onset zone, suggesting that bursts may represent the arrest of nascent seizures, making them prime candidates for false prediction. In the description below, a novel seizure prediction algorithm based on this method of EEG analysis is described. By isolating and modeling specific epochs of EEG associated with transition to seizure activity, predicting seizure onset in real time in a personalized manner not reliant on feature extraction is possible. Using data recorded from dogs with naturally occurring epilepsy demonstrate that this seizure prediction algorithm may represent a substantial improvement in prediction specificity with minimal on-line computational requirements.

In experimental studies, mixed hounds with spontaneous seizures were implanted with a continuous intracranial recording device designed and manufactured by NeuroVista Inc. (Seattle Wash.). Standard human-sized strip electrodes with a total of 16 contacts were implanted in the subdural space to cover both hemispheres of the canine neocortex (FIG. 1). All dogs had normal neurological examinations and MRI. The dogs were housed in the University of Minnesota canine epilepsy monitoring unit and continuously monitored (24 hours/day) with video and iEEG data.

Figure 7:
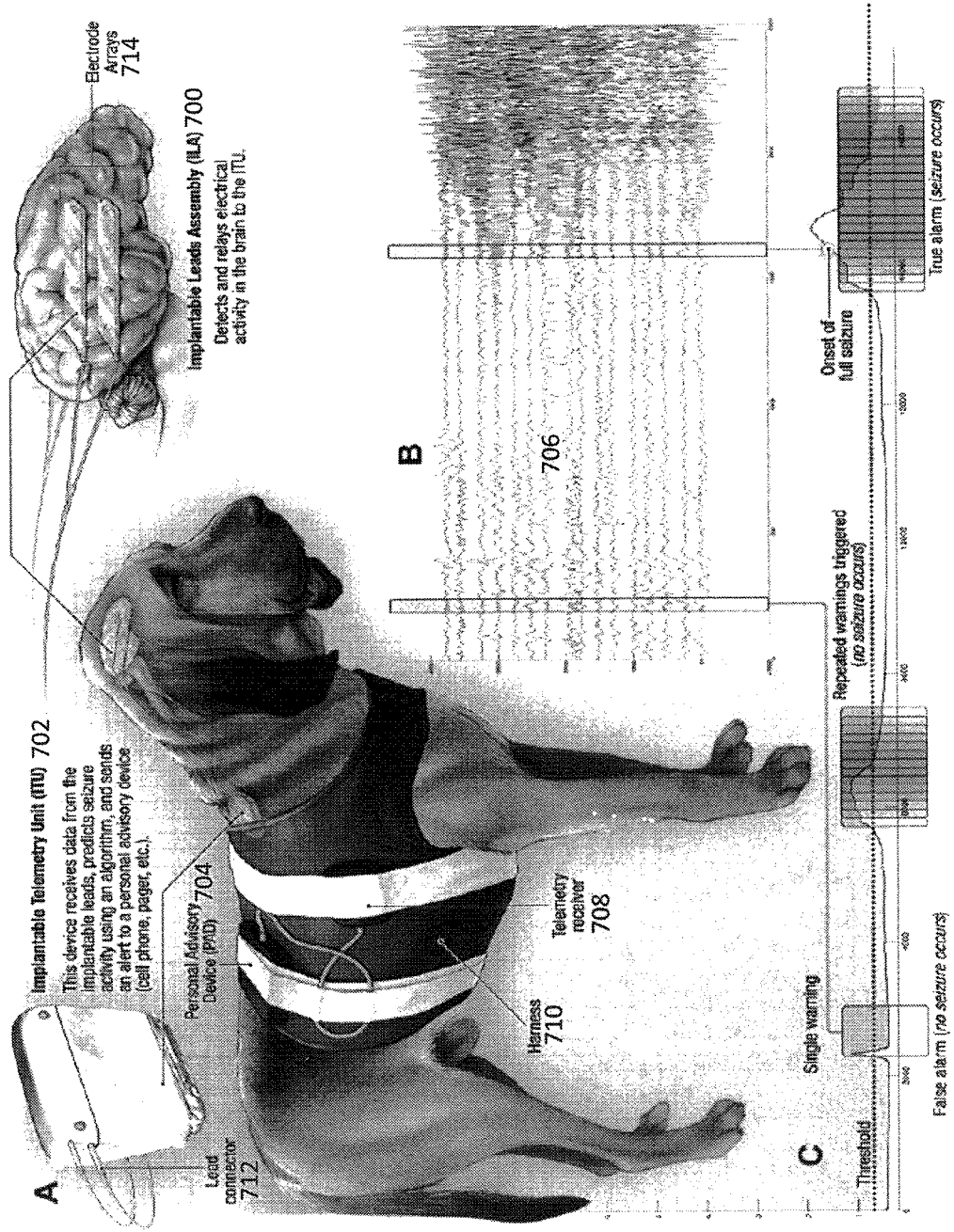
FIG. 7 is a diagram of a Seizure Advisory System (SAS) in a Dog with Epilepsy, according to an example embodiment.

The surgical technique and implanted device design are shown in FIG. 7. In FIG. 7, a Seizure Advisory System (SAS) was implanted in Canines with Epilepsy. The implantable device for recording and storing continuous iEEG signals includes an Implantable Lead Assembly (ILA) 700 including electrodes 714 placed in the subdural space (right), an Implantable Telemetry Unit (ITU) 702 including lead connectors 712, and both a Personal Advisory Device (PAD) 704 and telemetry receiver 708 mounted in dog harness 710. It should be noted that although PAD 704 and telemetry receiver 708 are dedicated devices that are mounted in the dog harness 710, both PAD 704 and telemetry receiver 708 may be substituted with another wireless device such as a smartphone that wirelessly communicates directly with ITU 702.

The system acquires 16 channels 706 of iEEG data and wirelessly transmits the data to the PAD via telemetry receiver 708. Data is stored on a flash drive on the PAD and uploaded weekly via the internet to a central data storage site. The sixteen channels of iEEG signals are recorded with the SAS. A focal onset, secondarily generalized seizure is shown. The top 1-8 channels are from the left hemisphere and 9-16 from the right hemisphere, as shown on the brain schematic above. The onset of the seizure is from left hemisphere electrodes 3 & 4.

This novel seizure prediction algorithm is designed to respond to the overall behavior of the EEG data rather than to extracted features. The model, which is described in detail below, uses a hidden Markov model (HMM) process to parse regions of the iEEG to different states, including the pre-seizure state. This method is applied to a training dataset in order to identify iEEG states characteristic of the immediate pre-seizure state and to optimize model parameters. These states are then approximated using Gaussian models to allow for real-time, unsupervised seizure prediction in a testing dataset.

In order to parse complex epileptic behavior into distinct dynamical regimes, a Bayesian nonparametric autoregressive Markov switching process was utilized. Due to the non-stationary behavior of iEEG, a time-varying autoregressive (AR) process is used to model each channel's activity. The model also mimics focal changes in iEEG by allowing for shared dynamical states among a variable number of iEEG channels and asynchronous state switching among channels.

Consider an event with N univariate time series of length T, with each individual time series being one of the iEEG voltage-recording channels. The scalar value for each channel I at each discrete time point t is denoted as $y_t^{(i)}$. Each channel is then modeled via Markov switches between a set of r-order auto-regressive dynamics. Denoting the latent state at time t by $$z_t^{(i)}$$

$$z_t^{(i)} \sim \pi_{z_{t-1}^{(i)}}^{(i)}$$

$$y_t^{(i)} = \sum_{j=1}^{r} a_{z_t^{(i)},j} y_{t-j}^{(i)} + \epsilon_t^{(i)} = a_{z_t^{(i)}}^T \tilde{y}_t^{(i)} + \epsilon_t^{(i)}$$

Equation (1)

Here, $a_k = (a_{k,1}, \ldots, a_{k,v})^T$ are the AR parameters for state k and $\pi_k$ is the transition distribution from state k to any other state. The notation $\tilde{y}_t^{(i)}$ as the vector of r previous observations $(y_{t-1}^{(i)}, \ldots, y_{t-r}^{(i)})^T$ is also introduced.

In contrast to a vector AR (VAR) HMM specification of the event, this modeling of channel dynamics separately allows for asynchronous switches and preserves individual channel information to permit sharing of dynamic parameters between recordings with a potentially different number of channels. Notably, the data is characterized by inter-channel correlations, which may change over time as the patient progresses through various seizure event states (e.g., "resting", "onset", "offset", etc.). That is, the channels may display one innovation covariance before a seizure (e.g., relatively independent and low-magnitude), but a different covariance during a seizure (e.g., correlated, higher magnitude). To capture this, the innovations $\epsilon_t = (\epsilon_t^{(1)}, \ldots, \epsilon_t^{(N)})^T$ are jointly modeled driving the AR-HMMs of Equation (1) as:

$$Z_t \sim \phi_{Z_{t-1}},$$

$$\epsilon_t \sim \mathcal{N}(0, \Delta_{Z_t}),$$

Equation (2)

where $Z_t$ denotes a Markov-evolving event state distinct from the individual channel states $\{z_t^{(i)}\}$, $\phi_l$ the transition distributions, and $\Delta_k$ the event-state-specific channel covariance. That is each $\Delta_l$ describes a different set of channel relationships.

For compactness:

$$y_t = A_{Z_t} \tilde{Y}_t + \epsilon_t(Z_t),$$

Equation (3)

where $y_t$ is the concatenation of N channel observations at time t and $z_t$ is the vector of concatenated channel states. The overall dynamic model is represented graphically in FIG. 10 which shows a graphical model of the factorial AR-HMM. The N channel states $z_t^{(i)}$ evolve according to independent Markov processes (transition distributions omitted for simplicity) and index the AR dynamic parameters $a_k$ used in generating observation $y_t^{(i)}$. The Markov-evolving event state $Z_t$ indexes the graph-structured covariance $\Delta_t$ of the correlated AR innovations resulting in multivariate observations $y_t = [y_t^{(1)}, \ldots, y_t^{(N)}]^T$ sharing the same conditional independencies.

To scale the model to a large number of channels, a Gaussian graphical model (GGM) for $\epsilon_t$ capturing a sparse dependency structure amongst the channels is considered. Let G=(V,E) be an undirected graph with V the set of channel nodes i and E the set of edges with (i,j)∈E if i and j are connected by an edge in the graph. Then, $[\Delta_l^{-1}]_{ij}=0$ for all (i, j)∉E, implying $\epsilon_t^{(i)}$ is conditionally independent $\epsilon_t^{(j)}$ of given $\epsilon_t^{(k)}$ for all channels k≠i,j. In the dynamic model of Equation (1), statements of conditional independence of $\epsilon_t$ translate directly to statements of the observations $y_t$.

G is chosen based on the spatial adjacencies of channels in the electrode grid. In addition to encoding the spatial proximities of iEEG electrodes, the graphical model also yields a sparse precision matrix $\Delta_l^{-1}$ allowing for more efficient scaling to the large number of channels commonly present in iEEG.

The formulation involves N+1 independently evolving Markov chains: N chains for the channel states $z_t^{(i)}$ plus one for the event state sequence $Z_t$. As indicated by the observation model of Equation (3), the N+1 Markov chains jointly generate observation vector $y_t$ leading to an interpretation of the formulation as a factorial HMM. However, there is a sparse dependency structure in how the Markov chains influence a given observation $y_t$ as induced by the conditional independencies in $\epsilon_t$ encoded in the graph G. That is, $y_t^{(i)}$ only depends on $Z_t$ the set of $z_t^{(j)}$ for which j is a neighbor of i in G.

As in the AR-HMM, a multivariate normal prior is placed on the AR coefficients as:

$$a_k \sim \mathcal{N}(m_0, \Sigma_0),$$

Equation (4)

with mean $m_0$ and covariance $\Sigma_0$. Throughout this work, let $m_0 = 0$.

For the channel covariance's $\Delta_l$ with sparse precisions $\Delta_l^{-1}$ determined by the graph G, a hyper-inverse Wishart (HIW) prior is specified as:

$$\Delta_l \sim HIW_G(b_0, D_0),$$

Equation (5)

where $b_0$ denotes the degrees of freedom and $D_0$ the scale. The HIW prior enforces hyper-Markov conditions specified by G.

Similar dynamics in the channels (sharing of AR processes) are expected, but also some differences are expected. For example, maybe only some of the channels ever get excited into a certain state. To capture this structure, a Bayesian nonparametric approach is taken, building on the beta process (BP) AR-HMM. Through the beta process prior, the BP-AR-HMM defines a shared library of indefinitely many AR coefficients $\{a_k\}$, but encourages each channel to use only a sparse subset of them.

The BP-AR-HMM specifically defines a feature model. Let $f^{(i)}$ be a binary feature vector associated with channel i with $f_k^{(i)}=1$ indicating that channel i uses the dynamic described by $a_k$. Formally, the feature assignments $f_k^{(i)}$ and their corresponding parameters $a_k$ are generated by a beta process random measure and the conjugate Bernoulli process (BeP) as:

$$B \sim BP(1, B_0)$$

$$X^{(i)} \sim BeP(B),$$

(Equation 6)

with base measure $B_0$ over the parameter space $\Theta = \mathbb{R}^r$ for the r-order autoregressive parameters $a_k$. As specified in Equation (4), take the normalized measure $B_0/\bar{B}_0$ ($\Theta$) to be $\mathcal{N}(m_0, \Sigma_0)$. The discrete measures B and $X^{(i)}$ can be represented as:

$$B = \sum_{k=1}^{\infty} \omega_k \delta_{a_k}, \quad X^{(i)} = \sum_{k=1}^{\infty} f_k^{(i)} \delta_{a_k},$$

Equation (7)

with $f_k^{(i)} \sim Ber(\omega_k)$. The resulting feature vectors $f^{(i)}$ constrain the set of available states that $z_t^{(i)}$ can take by constraining each transition distributions, $\pi_j^{(i)}$, to be 0 when $f_k^{(i)}=0$.

Specifically, the BP-AR-HMM defines $\pi_j^{(i)}$ by introducing a set of gamma random variables, $\eta_{jk}^{(i)}$, and setting:

$$\eta_{jk}^{(i)} \sim \text{Gamma}(\gamma_c + \kappa_c \delta(j, k)) \quad \text{Equation (8 and 9)}$$

$$\pi_j^{(i)} = \frac{\eta_j^{(i)} \circ f^{(i)}}{\sum_{k|f_k^{(i)}=1} \eta_{jk}^{(i)}}.$$

The positive elements of $\pi_j^{(i)}$ can also be thought of as a sample from a finite Dirichlet distribution with $K^{(i)}$ dimensions, where $K^{(i)} = \Sigma_k f_k^{(i)}$ represents the number of states channel i uses. For convenience, sometimes it denotes the set of transition variables $\{\eta_{jk}^{(i)}\}_j$ as $\eta^{(i)}$. As in the sticky HDP-HMM, the parameter $\kappa_c$ encourages self-transitions (i.e., state j at time t−1 to state j at time t).

A Bayesian non-parametric approach is taken to define the event state HMM, building on the sticky HDP-HMM. In particular, the transition distributions $\phi_t$ are hierarchically defined as:

$$\beta \sim \text{stick}(\alpha),$$

$$\phi_t \sim DP(\alpha_e \beta + \kappa_e e_l, \quad \text{Equation (10)}$$

where stick ($\alpha$) refers to a stick-breaking measure, also known as GEM ($\alpha$), where:

$$\beta'_k \sim \text{Beta}(1, \alpha), \quad k = 1, 2, \ldots, \quad \text{Equation (11)}$$

$$\beta_k = \beta'_k \prod_{\ell=1}^{k-1}(1-\beta'_\ell), \quad k = 1, 2, \ldots,$$

$$= \beta'_k \left(1 - \sum_{\ell=1}^{k-1} \beta_\ell\right) \quad k = 1, 2, \ldots$$

Again, the sticky parameter $\kappa_e$ promotes self-transitions, reducing state redundancy.

This model is termed the sparse factorial BP-AR-HMM. Although the graph G can be arbitrarily structured, because of the motivating seizure modeling application with a focus on a spatial-based graph structure, the sparse factorial BP-AR-HMM is described as capturing spatial correlations.

Figure 11:
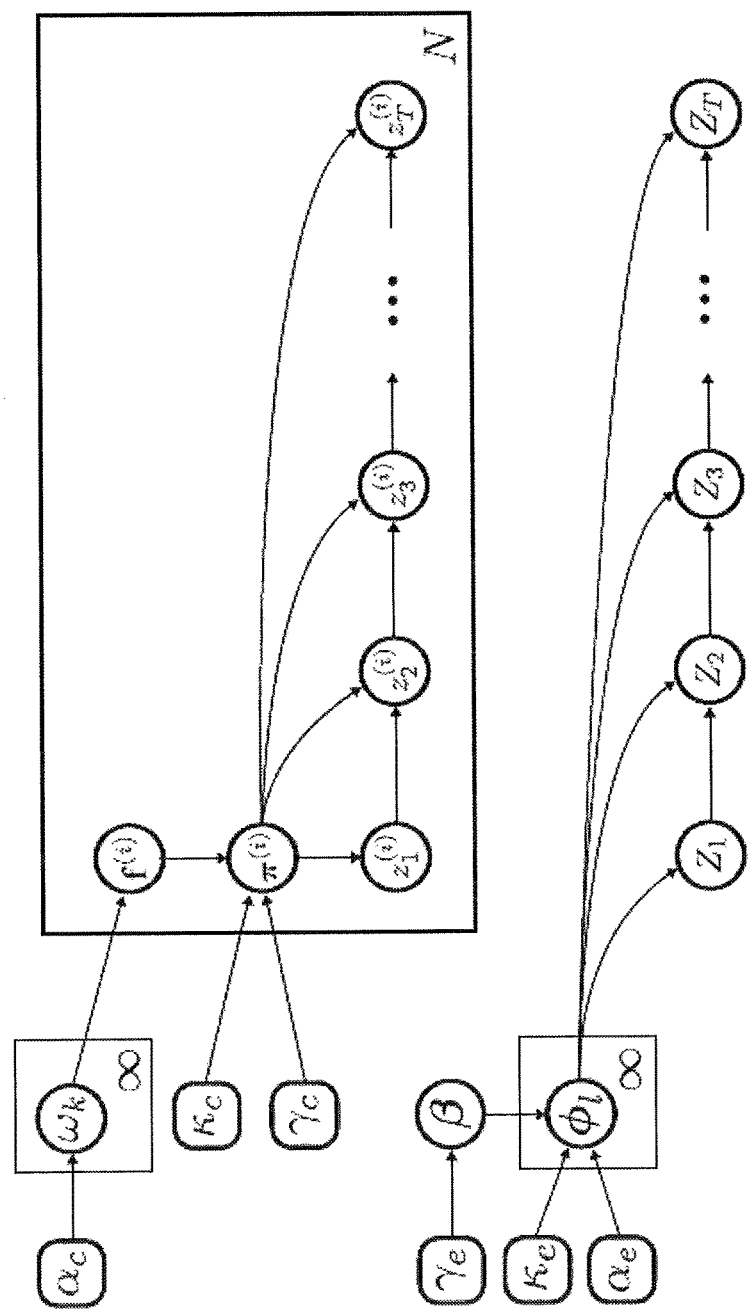
FIG. 11 is a graphical model that references the channel state and the event states sequences in FIG. 10.

This model is depicted in the directed acyclic graphs shown in FIG. 11. Note that while a model of only a single event is considered for notational simplicity, the formulation scales straightforwardly to multiple independent events. In this case, everything except the library of AR states $\{a_k\}$ becomes event-specific. If all events share the same channel setup, it is assumed that the channel covariance's $\{\Delta_l\}$ are shared as well.

Although the components of the model related to the individual channel dynamics are similar to those in the BP-AR-HMM, the posterior computations are significantly different due to the coupling of the Markov chains via the correlated innovations $\in_t$. In the BP-AR-HMM, conditioned on the feature assignments, each time series is independent. Here, however, a factorial HMM structure and the associated challenges are faced. Yet the underlying graph structure of the channel dependencies mitigates the scale of these challenges.

Figure 10:
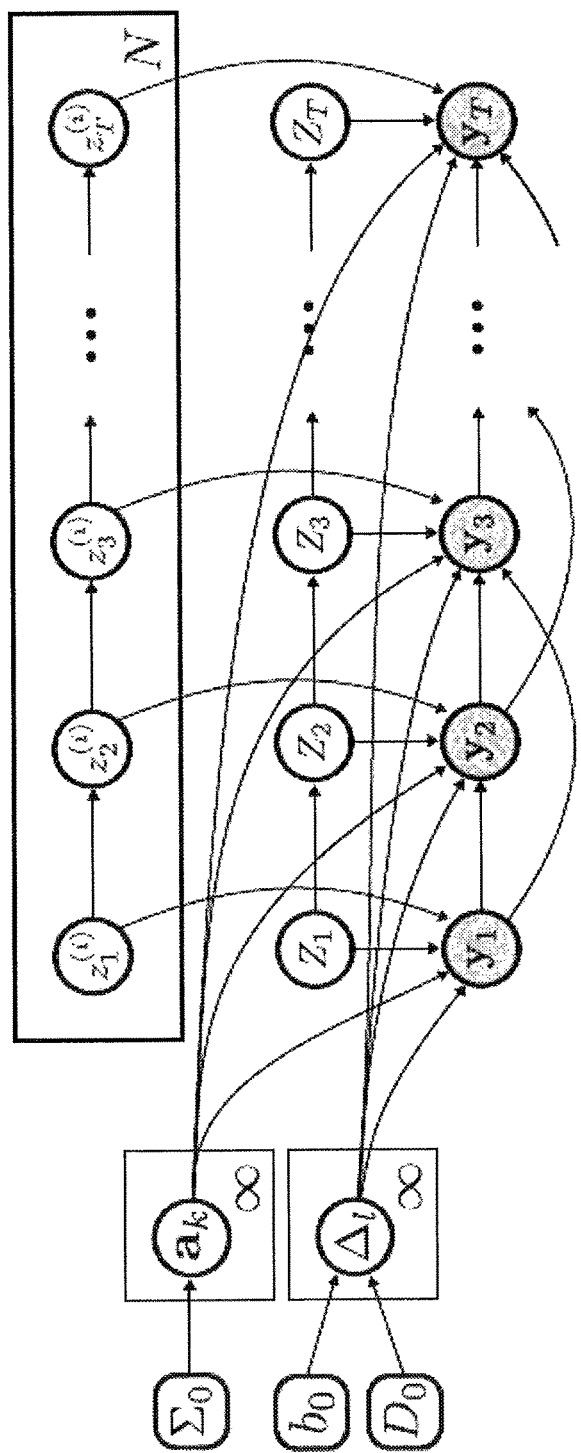
FIG. 10 is a graphical model of a factorial AR-HMM, according to an example embodiment.

It should be noted that FIG. 11 is a flowchart referencing the channel state and event state sequences of FIG. 10, here the graphical model associated with the Bayesian nonparametric prior specification is depicted. The channel i feature indicators $f^{(i)}$ are samples from a Bernoulli process with weights ($\omega_j$) and constrain the channel transition distributions $\pi^{(i)}$. Channel states $z_t^{(i)}$ evolve independently for each channel according to these feature-constrained transition distributions $\pi^{(i)}$. The event state $Z_t$ evolves independently of each channel i's state $z_t^{(i)}$ according to transition distributions $\{\phi_i\}$ which are coupled by global transition distribution $\beta$.

Table 1 describes an algorithm 1 (pseudo-code) for a sparse factorial BP-AR-HMM master Markov Chain Monte Carlo (MCMC) sampler:

TABLE 1

1:   for each MCMC iteration do
2:     get a random permutation h of the channel indices,
3:     for each channel i∈ h do
4:       sample feature indicators $f^{(i)}$ as in Equation (12)
5:       sample state sequence $z_{1:T}^{(i)}$ as in Equation (13)
6:       sample state transition parameters $\eta^{(i)}$ as in Equation (14)
7:     end for
8:     sample event states sequence $Z_{1:T}$
9:     sample event state transition parameters ø as in Equation (17)
10:     sample channel AR parameters $\{a_k\}$ as in Equation (19)
11:     sample channel $\{\Delta_l\}$ as in Equation (18)
12:     (sample hyper parameters $\gamma_c$, $\kappa_c$, $\alpha_e$, $\kappa_e$, $\gamma_e$, and $\alpha_c = B_0(\Theta)$)
13:   end for Conditioned on channel sequences $\{z_{1:T}^{(i')}\}$, $z_{1:T}^{(i)}$ can be marginalized, because of the graph structure, conditioning on a sparse set of other channels i' (i.e., neighbors of channel i in the graph) is performed. This step is beneficial for efficiently sampling the feature assignments $f^{(i)}$.

At a high level, each MCMC iteration proceeds through sampling channel states, events states, dynamic model parameters, and hyper parameters. Algorithm 1 summarizes these steps, which are described below.

Individual channel variables. The marginal likelihood of $y_{1:T}$ given $f^{(i)}$ and the neighborhood set of other channels $z_{1:T}^{(i')}$ is utilized in order to block sample $\{f^{(i)}, z_{1:T}^{(i)}\}$. That is, $f^{(i)}$ first sampled, thereby marginalizing $z_{1:T}^{(i)}$ and then sample $z_{1:T}^{(i)}$ given the sampled $f^{(i)}$. Sampling the active features $f^{(i)}$ for channel i uses an Indian buffet process (IBP) predictive representation associated with the beta process, but using a likelihood term that conditions on neighboring channel state sequences $z_{1:T}^{(i')}$ and observations $y_{1:T}^{(i')}$. Event state sequence $Z_{1:T}$ is used as a condition to define the sequence of distributions on the innovations. Generically, this yields:

$$p(f_k^{(i)}|y_{1:T}^{(i)}, y_{1:T}^{(i')}, z_{1:T}^{(i')}, Z_{1:T}, F^{-ik}, \eta^{(i)}, \{a_k\}, \{\Delta_l\}) \propto p(f_k^{(i)}|F^{-ik})p(y_{1:T}^{(i)}|y_{1:T}^{(i')}, z_{1:T}^{(i')}, Z_{1:T}, F^{-ik}, f_k^{(i)}, \eta^{(i)}, \{a_k\}, \{\Delta_l\}) \quad \text{Equation (12)}$$

Here, $F^{-ik}$ denotes the set of feature assignments not including $f_k^{(i)}$. The first term is given by the IBP prior and the second term is the marginal conditional likelihood (marginalizing $z_{1:T}^{(i)}$). Based on the derived marginal conditional likelihood, feature sampling follows.

Conditioned on $f^{(i)}$ the state sequence $z_{1:T}^{(i)}$ is block sampled using a backward filtering forward sampling algorithm based on a decomposition of the full conditional as:

$$p(z_{1:T}^{(i)}|y_{1:T}^{(i)}, y_{1:T}^{(i')}, z_{1:T}^{(i')}, f^{(i)}, \eta^{(i)}, \{a_k\}, \{\Delta_l\}) = p(z_1^{(i)}|y_1^{(i)}, y_1^{(i')}, z_1^{(i')}, f^{(i)}, \eta^{(i)}, \{a_k\}, \{\Delta_l\}). \quad \text{Equation (13)}$$

$$\prod_{t=2}^{T} p(z_i^{(i)} \mid y_{t:T}^{(i)}, y_{t:T}^{(i')}, z_{t-1}^{(i)}, z_{t:T}^{(i')}, f^{(i)}, \eta^{(i)}, \{a_k\}, \{\Delta_l\})$$

For sampling the transition parameters $\eta^{(i)}$ sampling is performed from the full conditional:

$$p(\eta_{jk}^{(i)} \mid z_{1:T}^{(i)}, f_k^{(i)}) \propto \frac{(\eta_{jk}^{(i)})^{n_{jk}^{(i)} + \gamma_c + \kappa_c \delta(j,k) - 1} e^{\eta_{jk}^{(i)}}}{\sum_{k' \mid f_{k'}^{(i)} = 1} \eta_{jk'}^{(i)}},$$  Equation (14)

where $n_{jk}^{(i)}$ denotes the number of times channel i transitions from state j to state k. $\eta_j^{(i)} = C_j^{(i)} \overline{\eta}_j^{(i)}$ is sampled from its posterior via two auxiliary variables:

$$\overline{\eta}_j^{(i)} \sim \mathrm{Dir}(\gamma_c + e_j \kappa_c + n_j^{(i)})$$

$$C_j^{(i)} \sim \mathrm{Gamma}(K\gamma_c + \kappa_c, 1),$$  Equation (15)

where $n_j^{(i)}$ gives the transition counts from state j in channel i.

Conditioned on the channel state sequences $z_{1:T}$ and AR coefficients $\{a_k\}$, innovations sequence is computed as $\in_t = y_t - A_{Z_t} \check{Y}_t$, where the definition of $A_k$ and $\check{Y}_t$ are taken from Equation (3). These innovations are the observations of the sticky HDP-HMM of Equation (2). For simplicity and to allow block-sampling of $z_{1:T}$, a weak limit approximation of the sticky HDP-HMM is considered. The top-level Dirichlet process is approximated by an L-dimensional Dirichlet distribution, inducing a finite Dirichlet for $\phi_l$:

$$\beta \sim \mathrm{Dir}(\gamma_e/L, \ldots, \gamma_0/L),$$

$$\phi_l \sim \mathrm{Dir}(\alpha_k \beta + \kappa_e e_l).$$  Equation (16)

Here, L provides an upper bound on the number of states in the HDP-HMM. The weak limit approximation still encourages using a subset of these L states.

Based on the weak limit approximation, the parent transition distribution $\beta$ is first sampled, followed by sampling each $\phi_l$ from its Dirichlet posterior:

$$p(\phi_l \mid Z_{1:T}, \beta) \propto \mathrm{Dir}(\alpha_e \beta + e_l \kappa_e + n_l),$$  Equation (17)

where $n_l$ is a vector of transition counts of $Z_{1:T}$ from state l to the L different states.

Using standard conjugacy results, based on "observations" $\in_t = y_t - A_{Z_t} \check{Y}_t$ for t such that $Z_t = l$, the full conditional probability for $\Delta_l$ is given by:

$$p(\Delta_l \mid y_{1:T}, z_{1:T}, Z_{1:T}, \{a_k\}) \propto HIW_G(b_l, D_l),$$  Equation (18)

where, $b_l = b_0 + |\{t \mid Z_t = l, t = 1, \ldots, T\}|,$ $D_l = D_0 + \sum_{t \mid Z_t = l} \varepsilon_i \varepsilon_i^T.$ Conditioned on the truncated HDP-HMM event transition distributions $\{\phi_l\}$ and emission parameters $\{\Delta_l\}$ a standard backward filtering forward sampling scheme is used to block sample $Z_{1:T}$.

Each observation $y_t$ is generated based on a matrix of AR parameters $A_{Z_t} = [a_{Z_t}^{(r)} | \ldots | a_{Z_t}^{(N)}]$. Thus, sampling $a_k$ involves conditioning on $\{a_{k'}\}_{k' \ne k}$ and disentangling the contribution of $a_k$ on each $y_t$. The full conditional for $a_k$ is a multivariate normal:

Equation (19)

$$p(a_k \mid y_{1:T}, z_{1:T}, Z_{1:T}, \{a_{k'}\}_{k' \ne k}, \{\Delta_l\}) \propto \mathcal{N}(\mu_k, \Sigma_k),$$

where, $$\Sigma_k^{-1} = \Sigma_0^{-1} + \sum_{t=1}^{T} \overline{Y}_i^{(k^+)} \Delta_{Z_i}^{-1(k^+, k^+)} (\overline{Y}_t^{(k^+)})^T,$$

$$\Sigma_k^{-1} \mu_k = \sum_{t=1}^{T} \overline{Y}_i^{(k^+)} (\Delta_{Z_t}^{-i(k^+, k^+)} y_i^{(k^+)} + \Delta_{Z_i}^{-i(k^+, k^-)} \varepsilon_i^{(k^-)}).$$

The vectors $k^-$ and $k^+$ denote the indices of channels assigned and not assigned to state k at time t, respectively. These are used to index into the rows and columns of the vectors $\in_t$, $y_t$ and matrix $\Delta_{Z_t}$. Each column of matrix $\overline{Y}_t^{(k^+)}$ is the previous r observations for one of the channels assigned to state k at time t. It is noted that equation 19 describes a distribution governing parameters of the autoregressive model and is used to parse the iEEG signal into event states.

While the AR-HMM determines a dynamical state at each time point for each individual channel, in this experimentation the overall event states are relied upon in order to capture global brain dynamics. Preliminary studies using this model to parse seizure activity demonstrated successful characterization of seizure dynamics, with identification of dynamical transitions in agreement with those identified manually by a board-certified epileptologist (FIG. 2).

Figure 2:
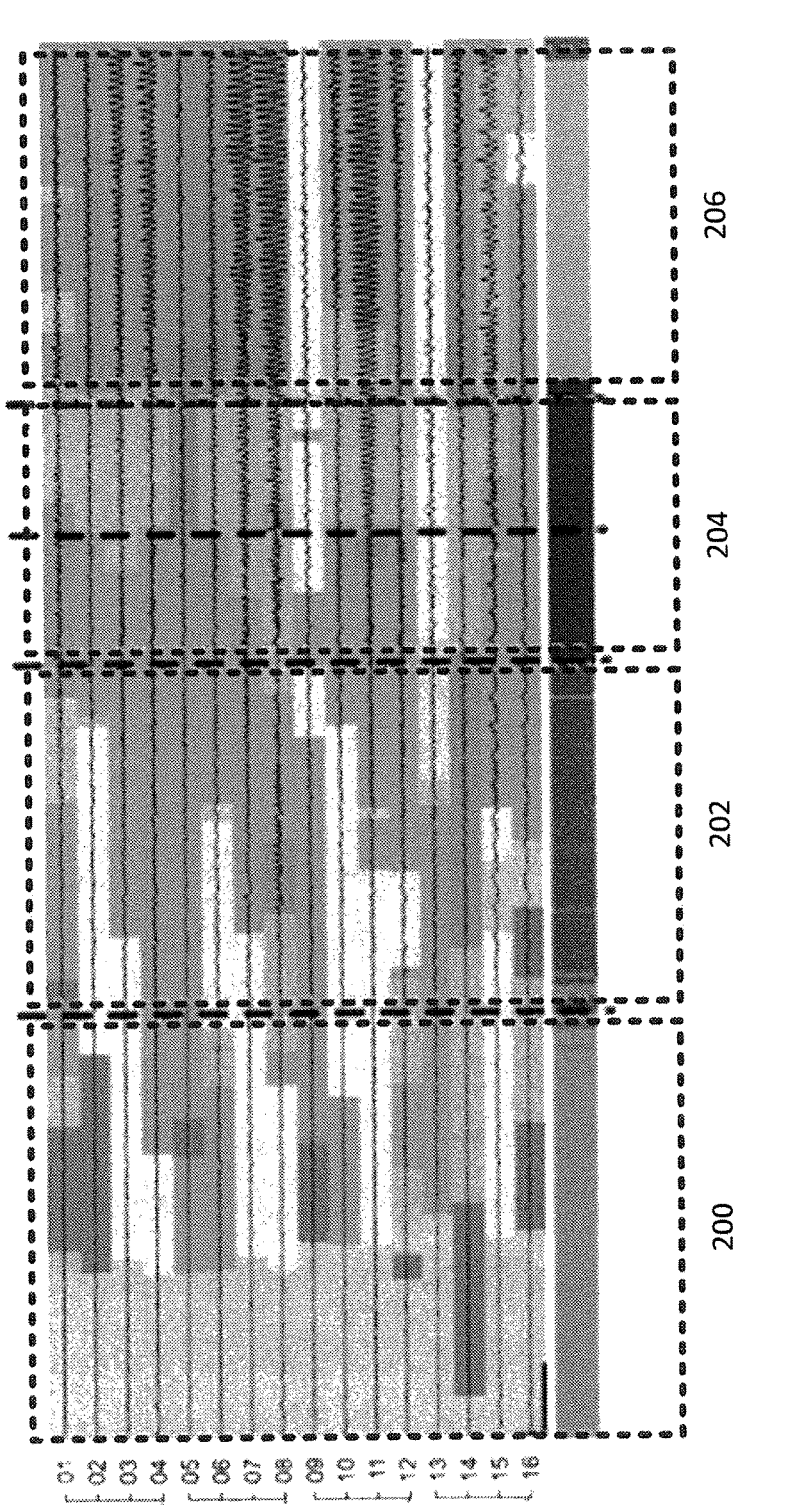
FIG. 2 is a data plot showing data traces from the 16 channel iEEG electrode over 25 seconds of a seizure onset with multiple inferred channel states, according to an example embodiment.

It should be noted that FIG. 2 shows data traces from the 16 channel iEEG electrode over 25 seconds of a seizure onset with multiple inferred channel states 200, 202, 204 and 206. Vertical dashed lines indicate the iEEG transition times marked independently by an epileptologist.

Using this AR-HMM, each time point of iEEG data was parsed into one of 30 event states. The number of event states was empirically chosen to capture a sufficiently wide range of iEEG behaviors. Potential States of Interest (SOI) were identified by investigating which event states were disproportionately enriched in pre-seizure zones, defined as the 30 second window prior to the unequivocal epileptic onset (UEO) for each seizure. The UEO is defined as the earliest time that seizure activity is evident to an epileptologist viewing iEEG data without prior knowledge of seizure occurrence.

Final SOIs were chosen by maximizing specificity (fewest out-of-zone appearances) and sensitivity (required appearance in all pre-seizure zones). The particular SOIs used in seizure prediction are personalized. They are derived through analysis of the individual subject's event states and are therefore tailored to the subject's particular form of seizure presentation. In each dog, 3 SOIs were identified with consistent appearance in pre-seizure zones with specificity>99%. However, the final number of SOIs chosen may vary among subjects based on individual seizure onset iEEG profiles. Notably, these SOIs were not found to occur more frequently during burst activity than at baseline (p=0.21).

Identification of pre-seizure SOIs may not be directly useful for real-time seizure prediction for several reasons. First, determination of event states for each time point by the AR-HMM requires the entire time series to be analyzed at once as the state determinations are not independent in time, thereby preventing predictive use. Second, determination of event states by this model is quite computationally intensive. Even if an approximate predictive model were designed, the hardware demands for such computation may render it unsuitable for use in an implantable device.

Therefore, in order to translate this approach into a real-time predictor, a model informed by existing AR-HMM event states is designed to predict future event states. This model accumulates all time points associated with each event state into separate data sets. This transformation provides one matrix for each event state of size N (the number of channels. In this case N=16) by M (the number of time points associated with the particular state). Each of these matrices was modeled as a Gaussian distribution, resulting in an N-dimensional vector mean (~) and an N×N covariance matrix (Σ) associated with each state (FIG. 3).

Figure 3:
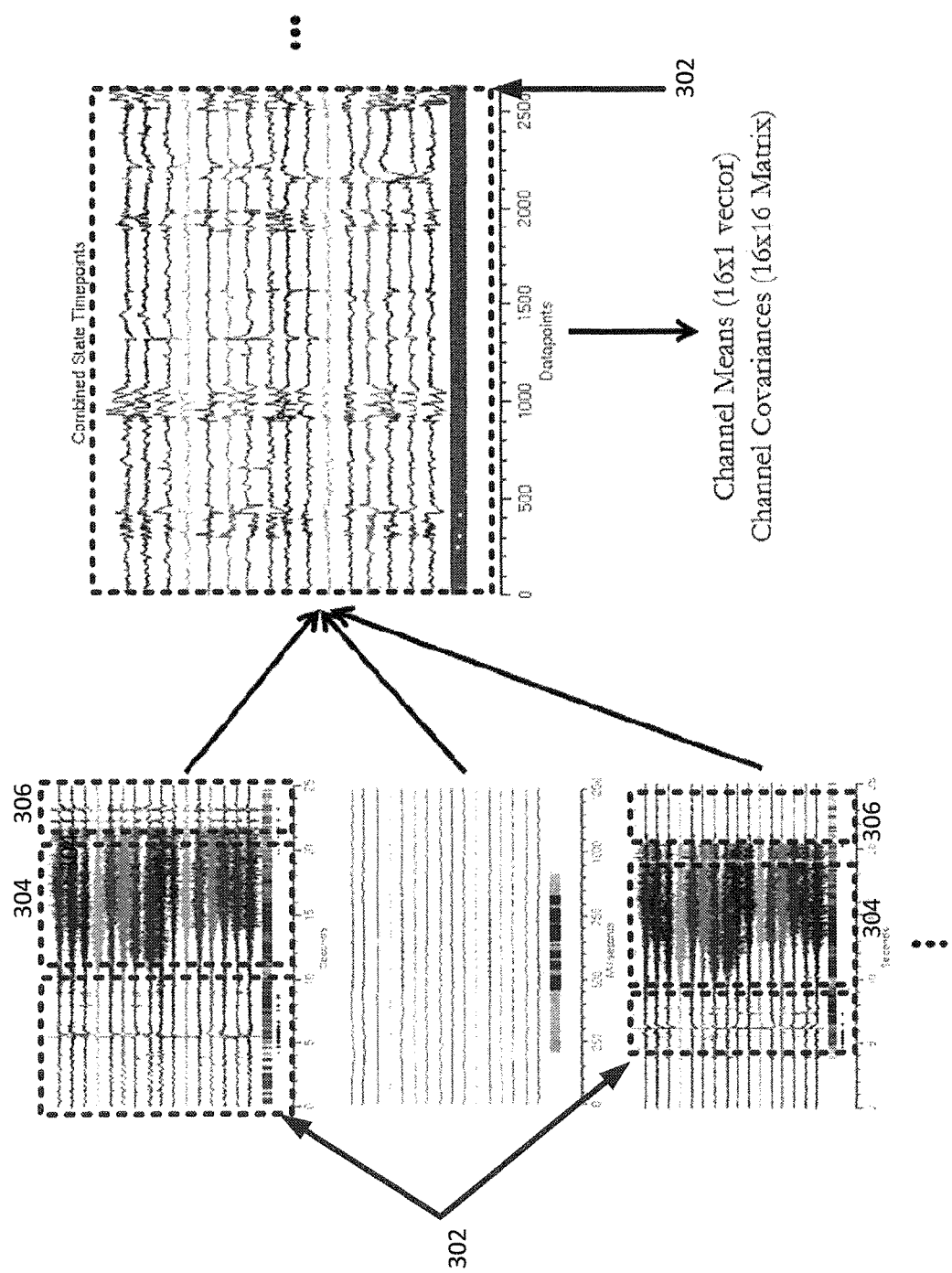
FIG. 3 is a data plot that is useful for describing the construction of Gaussian distributions, according to an example embodiment.

It is noted that FIG. 3 shows a schematic of construction of Gaussian distributions. Each time point in the training dataset is assigned an event state based on the AR-HMM. Three sample recording clips are shown, with time points coded by event state (e.g. 302, 304 and 306). The time points are then segregated by state to generate a unique dataset for each event state. These datasets are then modeled as a 16-dimensional Gaussian distribution. This approach provides a unique Gaussian distribution (with a 16-dimensional vector mean and a 16×16 covariance matrix) for each event state to model the iEEG signal in this state. Each dimension of this distribution describes the signal from a single recording electrode. FIG. 3 illustrates this operation for a single state 302.

If T is the N×t timeseries of multichannel iEEG data, $T_i$ is the timeseries for event state i, and V is the 1×t series of event states, $T_i$ may be denoted as:

$$T_i = T_t \forall V_t = i \quad \text{Equation 20}$$

The mean and covariance of each event state may be defined as:

$$\mu_i = E(T_i)$$

$$\Sigma_{ijk} = E[(T_j - \mu_j)(T_k - \mu_k)] \quad \text{Equation (21)}$$

where E represents the expected value function. The probability density function for the Gaussian distribution for each state is thus represented by:

$$p(X: \mu, \Sigma) = \frac{1}{2\pi^{n/2}|\Sigma|^{1/2}} e^{[-\frac{1}{2}(X-\mu)^T \Sigma^{-1}(X-\mu)]} \quad \text{Equation (22)}$$

These newly defined Gaussian distributions can then be used to calculate to which state an incoming time point would most likely belong. Through a matrix multiplication, the probability that incoming data (an N-dimensional vector of signal amplitude of each channel) was drawn from each of the state distributions can be determined, and the state assignment made using maximum likelihood estimation. This calculation allows for the assignment of data to approximated event states in real time with minimal computational overhead.

One potential complication of online seizure predictors is handling of imperfect data recording in the form of artifacts, often occurring due to slight shifting of the recording equipment relative to the brain. Artifacts typically appear as brief, irregular readings of extreme amplitude, often resulting in false positives for feature-based predictors. In the present model, additional event states were added to identify these artifacts. These states were generated by accumulating data points across 5-10 artifacts and modeling the data with a three-component Gaussian mixture model. Each of these components was then added to the model as an "artifact event state." Inclusion of these artifact event states enables the recognition of artifact-like behavior, preventing these recordings from being miscategorized into one of the 30 "real" event states.

Figure 4:
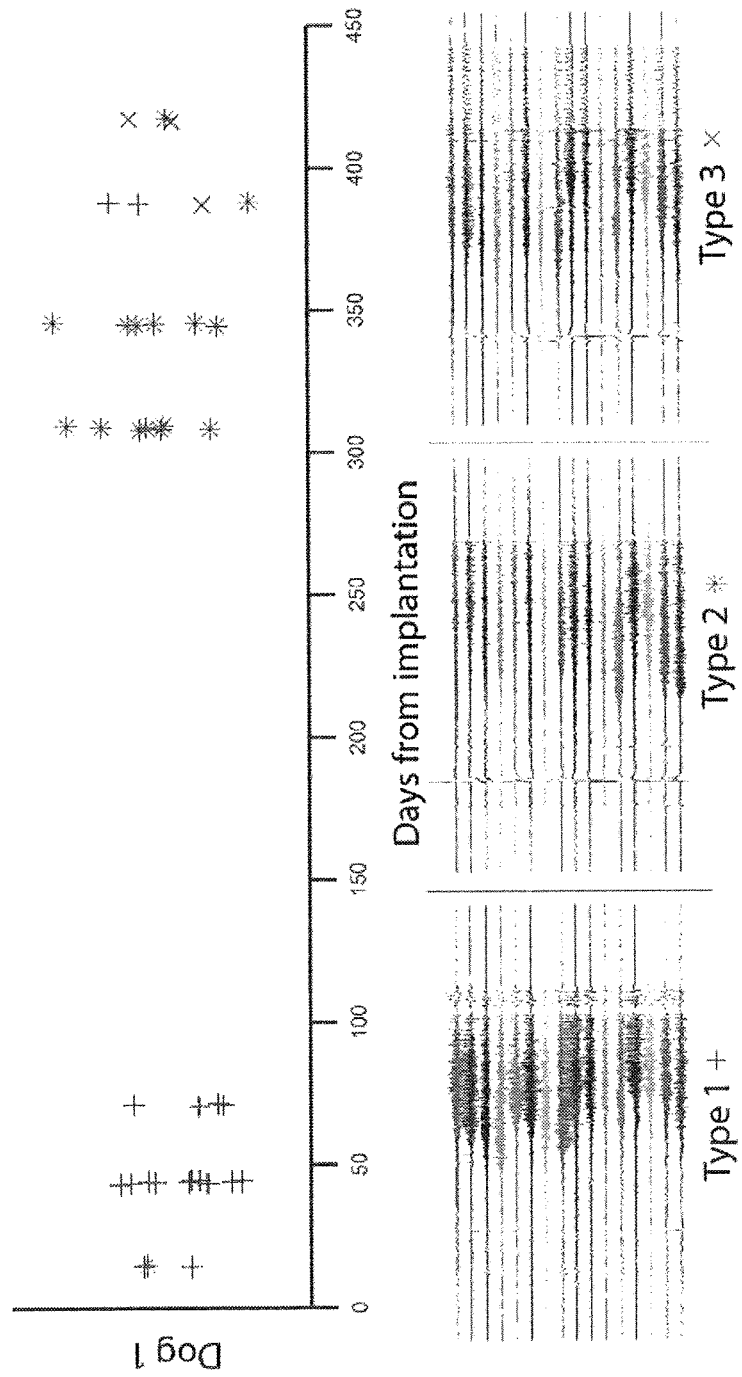
FIG. 4 is a data plot showing three categories of seizure patterns are demonstrated in Dog 1, according to an example embodiment.
Figure 5A:
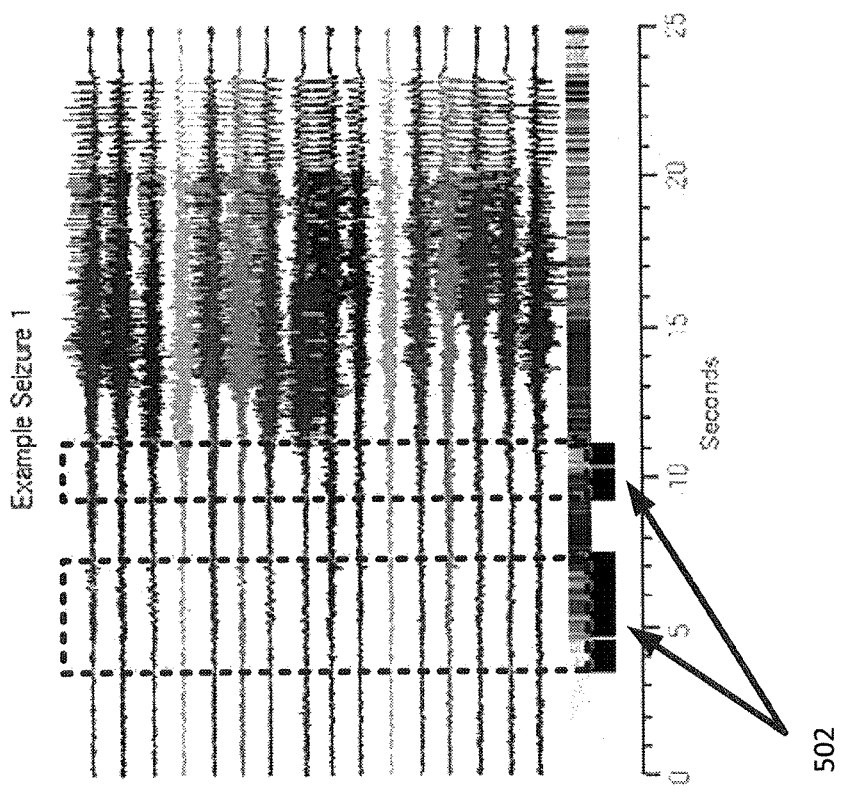
FIG. 5A is a data plot showing a first sample seizure from Dog 1, according to an example embodiment.
Figure 5B:
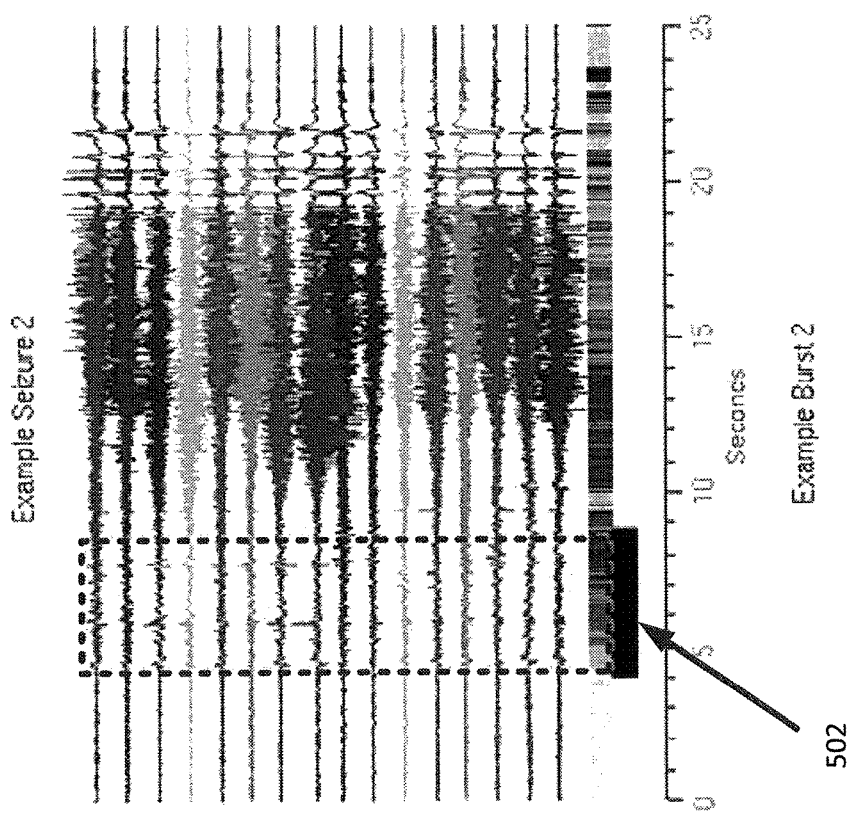
FIG. 5B is a data plot showing a second sample seizure from Dog 1, according to an example embodiment.
Figure 5C:
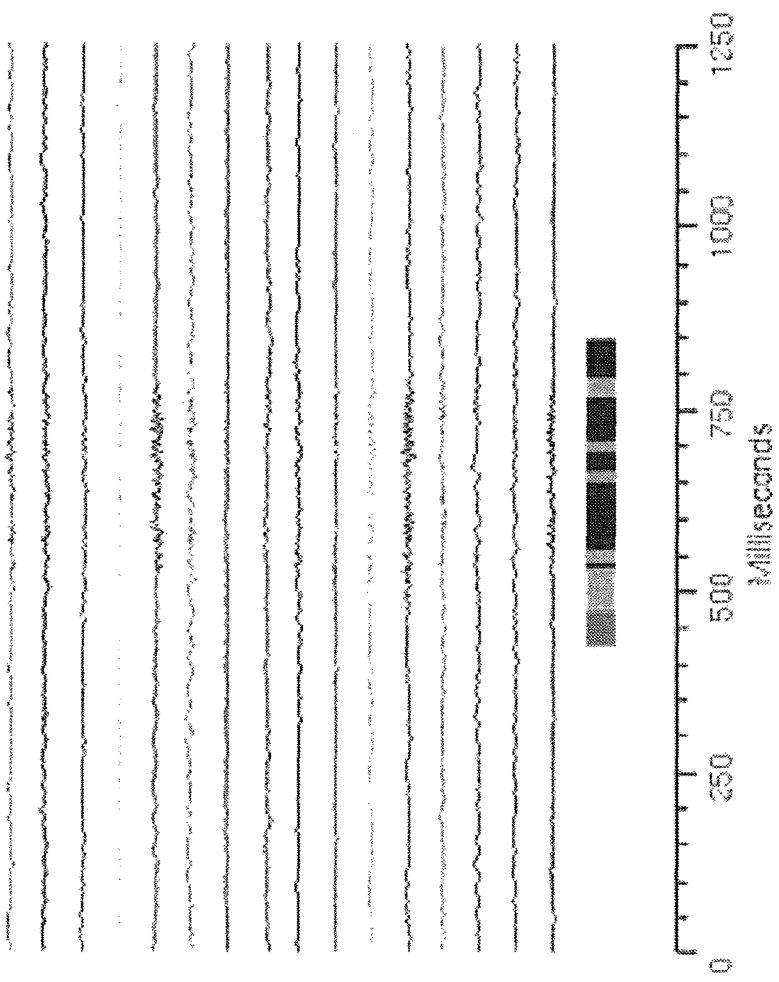
FIG. 5C is a data plot showing a first sample burst from Dog 1, according to an example embodiment.
Figure 5D:
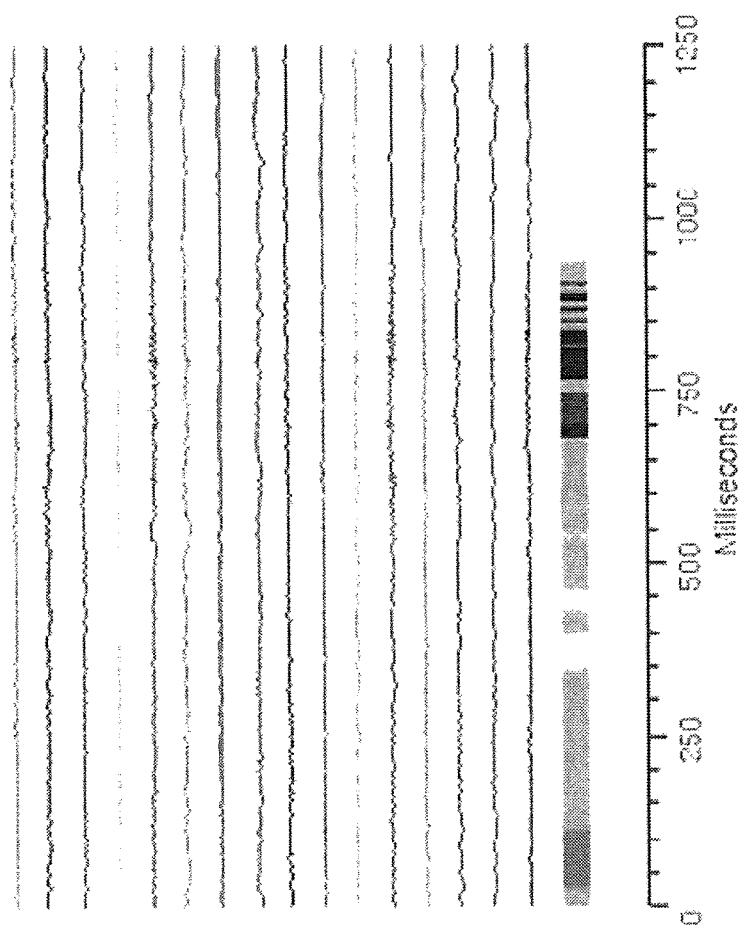
FIG. 5D is a data plot showing a second sample burst from Dog 1, according to an example embodiment.

Model testing was carried out to simulate online prediction. Each data set was sequentially segmented into a 30-day "burn-in period" to be discarded, a 60-day training data set, and the remainder to be used as a testing data set. The training period in Dog 1 contained 14 seizures and 61 bursts, while the training period in Dog 2 contained 12 seizures and 524 bursts. This segmentation produced a testing dataset for Dog 1 of length 337 days with 20 seizures and 407 bursts, and a testing dataset for Dog 2 of 54 days with 35 seizures and 389 bursts. It is important to note that each animal tested had multiple seizure onset types that, while falling into a range of similar morphologies, were variable enough in their temporal characteristics as to challenge standard seizure prediction algorithms. FIG. 4 depicts the range of seizure onset patterns in one test animal. It is noted that FIG. 4 shows seizure onset patterns and locations are variable over the course of the recordings. Three major categories of seizure patterns are demonstrated in Dog 1 as determined by manual review by an epileptologist. Each seizure type had a different initial onset location.

The training data set was used to determine true event states using the AR-HMM. These states were then used as described previously, to create the Gaussian models to be used for online prediction. Thus, the dataset used for algorithm testing was kept separate from all data used to inform the model. Pre-seizure states are identified based on a sliding window of incoming data. If the percentage of points within the window identified as SOIs exceeds a specified threshold, the predictor signals that a pre-seizure state is present. The specific window length and threshold value were optimized over the training data set by sampling the parameter space to provide the fewest false positives possible while ensuring that all seizures were predicted prior to the UEO (zero false negatives). In this testing, once a seizure is flagged, the predictor is deactivated for five minutes in order to prevent multiple predictions of the same event.

This method is demonstrated in FIGS. 5A-5D which shows sample seizures and bursts from Dog 1. Each time point is coded by real event state as determined by the AR-HMM. The same seizures and bursts were evaluated using the online Gaussian prediction method to determine approximate event states and to identify time points at which the most likely state is an SOI. Time points that fall in sliding windows in which the percentage of predicted SOIs exceeds a set threshold are marked with black bars 502. These windows are sensitive and specific for seizure onset zones.

A feature-based predictor modeled after the NeuroPace seizure prediction system was developed to serve as a control. This predictor was responsive to signal line length, halfwave, and area under the curve. Thresholds for each feature were determined graphically by plotting feature values over time in order to ensure that the threshold chosen was both sensitive and specific for seizure onset. The specific binary operations among the three features used to predict seizure onset were determined through optimization on the training data to limit false positives while preserving a false negative rate of zero.

The efficacy of each algorithm was assessed by the false negative and false positive rates, as well as the latency of each seizure call (Table 1). The latency was measured relative to the UEO of each seizure. Of the twenty seizures in the testing dataset for Dog 1, all twenty were predicted by both the HMM-Gaussian model and the feature-based predictor with average latencies of 12.1±69 seconds and 18.5±4.9 seconds before the marked UEO, respectively. Over the 337 days of recorded data, the HMM Gaussian model returned 5 false positives (6.2×10-4/hr; 0.25/seizure), while the feature-based predictor returned 116 false positives (1.4×10-2/hr; 5.8/seizure). For Dog 2, all thirty-five of the seizures were predicted by the HMM-Gaussian model with an average latency of 10.7±8.1 seconds before the UEO while the feature-based model predicted thirty-three of thirty-five with average latency of 19.0±12.7 seconds before the UEO. Over 54 days of recorded data, the HMM-Gaussian model returned 6 false positives (3×10-3/hr; 0.17/seizure) while the feature-based model returned 430 (0.21/hr; 12.3/seizure).

Over both dogs, the seizure flags by the HMM-Gaussian method ranged in latency from 4 to 24 seconds before the UEO. The feature-based model ranged from 8-23 seconds before the UEO. In Dog 1, the rate of false positives in the feature-based predictor (1.4×10-2/hr) matches the published rate of the NeuroPace device (1.3×10-2/hr), suggesting that this model is an appropriate control for comparison to devices used in practice.

In an effort to decrease false positives produced by the feature-based algorithm, the feature thresholds were revised to make the model more robust to bursts. Parameters were plotted as described above, and rather than selecting feature cutoffs based on baseline values, cutoffs were chosen to exceed the maximum activity seen during bursts in the training set. This revised model showed modestly improved false positive rates and slightly decreased latencies. In Dog 1, 71 false positives (8.8×10-3/hr; 3.55/seizure) were predicted with latency 15.7±3.8 seconds before the UEO. In Dog 2, 232 false positives (0.11/hr; 6.63/seizure) were predicted with latency 15.6±5.1 seconds before the UEO.

Table 2 shows performance metrics of HMM-Gaussian and feature-based methods. "Feature *" indicates that the method was trained specifically to limit false positives during bursts. FN=false negatives (missed seizures). FP=false positives. Latency is measured relative to UEO. It is noted that Table 2 shows that the performance metrics of the HMM-Gaussian model is similar to those of the state of the art Kaggle algorithm in both dogs. This demonstrates that the HMM-Gaussian method performs comparably to the state of the art predictor over these datasets.

TABLE 2

| Dog | Method | FN | FP (rate h$^{-1}$) | Latency (s) |
|---|---|---|---|---|
| 1 | HMM-Gaussian | 0 | 5 (6.2 × 10$^{-4}$) | −12.1 ± 6.9 |
| 1 | Feature | 0 | 116 (1.4 × 10$^{-2}$) | −18.5 ± 4.9 |
| 1 | Feature* | 0 | 71 (8.8 × 10$^{-3}$) | −15.7 ± 3.8 |
| 1 | Kaggle | 0 | 3 (3.7 × 10$^{-4}$) | −10.1 ± 5.5 |
| 2 | HMM-Gaussian | 0 | 6 (4.6 × 10$^{-3}$) | −10.7 ± 8.1 |
| 2 | Feature | 2 (0.057) | 430 (0.33) | −19.0 ± 12.7 |
| 2 | Feature* | 2 (0.057) | 232 (0.18) | −15.6 ± 5.1 |
| 2 | Kaggle | 0 | 7 (5.4 × 10$^{-3}$) | −8.6 ± 4.2 |

The high rate of false positives inherent in current feature-based prediction has hampered use of these systems in practice, as it is associated with unnecessary stimulation and decreased battery life. While both the feature-based and HMM-Gaussian predictors correctly identified all seizures in Dog 1 and the vast majority of seizures in Dog 2, the HMM-Gaussian predictor demonstrated a drastic reduction in false positive predictions. This finding provides a high level of confidence that the HMM-Gaussian predictor consistently identifies seizure onset zones before seizure generalization occurs, at a time when clinical intervention is possible. This belief is supported by the fact that the NeuroPace seizure predictor, which has shown a degree of efficacy in symptom suppression in practice (seizure reduction of 40% relative to baseline), has a published latency of 5.01 seconds after the UEO.

The seizure prediction algorithm is ideal for incorporation into an implantable device. All computationally difficult calculations are performed externally during model setup for analysis of training data. Categorization of incoming data into estimated event states in real time uses only a single matrix multiplication per data point, allowing for high time resolution sampling with minimal hardware requirements.

False positive predictions flagged by the feature-based predictor are not distributed at random throughout the recording. Rather, these calls are clustered in areas of high seizure activity. In particular, false positives tend to occur during or in close association with bursts (FIGS. 6A-6C), and retraining of the algorithm to limit prediction of bursts effected a significant reduction in false positives.

Figure 6A:
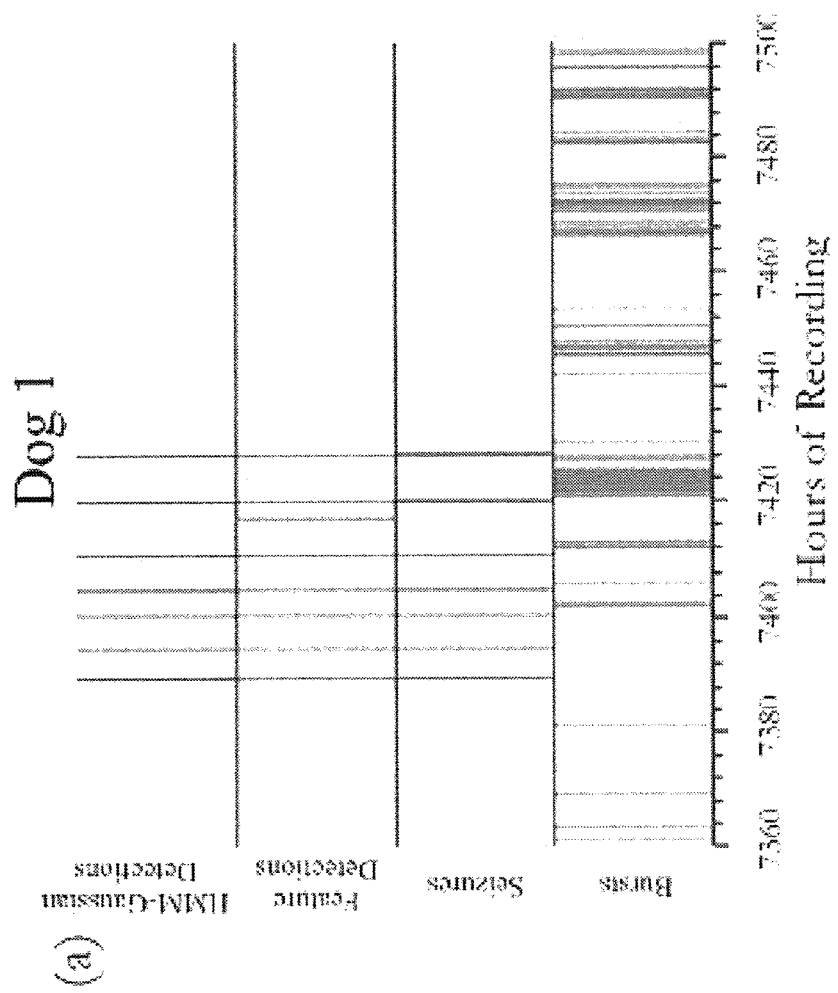
FIG. 6A is a data plot showing representative timeline excerpts from Dog 1, according to an example embodiment.
Figure 6B:
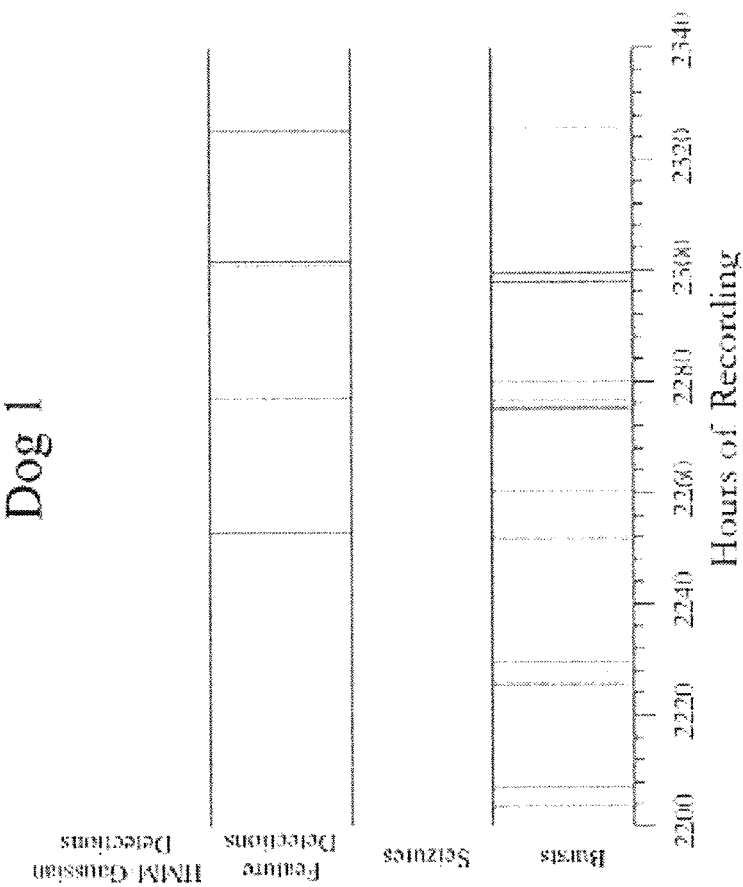
FIG. 6B is a data plot showing representative timeline excerpts from Dog 1, according to an example embodiment.
Figure 6C:
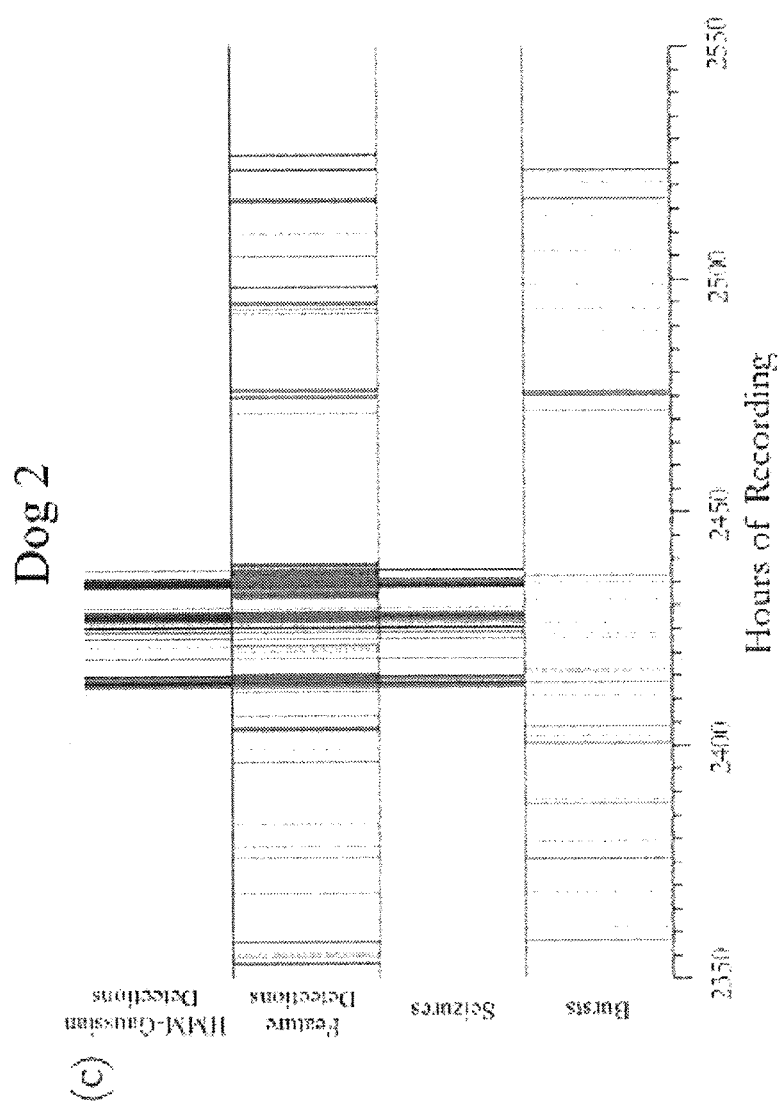
FIG. 6C is a data plot showing representative timeline excerpts from Dog 2, according to an example embodiment.

It is noted that FIGS. 6A-6C shows representative timeline excerpts from Dog 1, and Dog 2. The top row represents predicted seizures by the HMM-Gaussian predictor, the second row represents predicted seizures by the feature-based, NeuroPace-like predictor, the third row represents real seizures, and the bottom row represents real bursts. Note that false positives flagged by the NeuroPace-like predictor tend to cluster with interictal bursts.

In contrast, the HMM-Gaussian seizure predictor is based on identification of event states that are specifically chosen to be absent from bursts and surrounding background. This method greatly increases robustness to bursts, thereby eliminating a major source of false positive readings. In addition to accomplishing reliable seizure prediction with greatly reduced false positive rate, it is shown that it is possible to identify specific epochs of iEEG behavior that are useful for distinguishing bursts from nascent seizures.

Interaction between the computationally intensive training method and its low-computational overhead implementation suitable for an implantable devices is worthy of comment. With increasing availability of central, cloud-based computational and data integration, collection of data from individual devices, central training, and periodic updates of implantable devices is now a reality.

Figure 8:
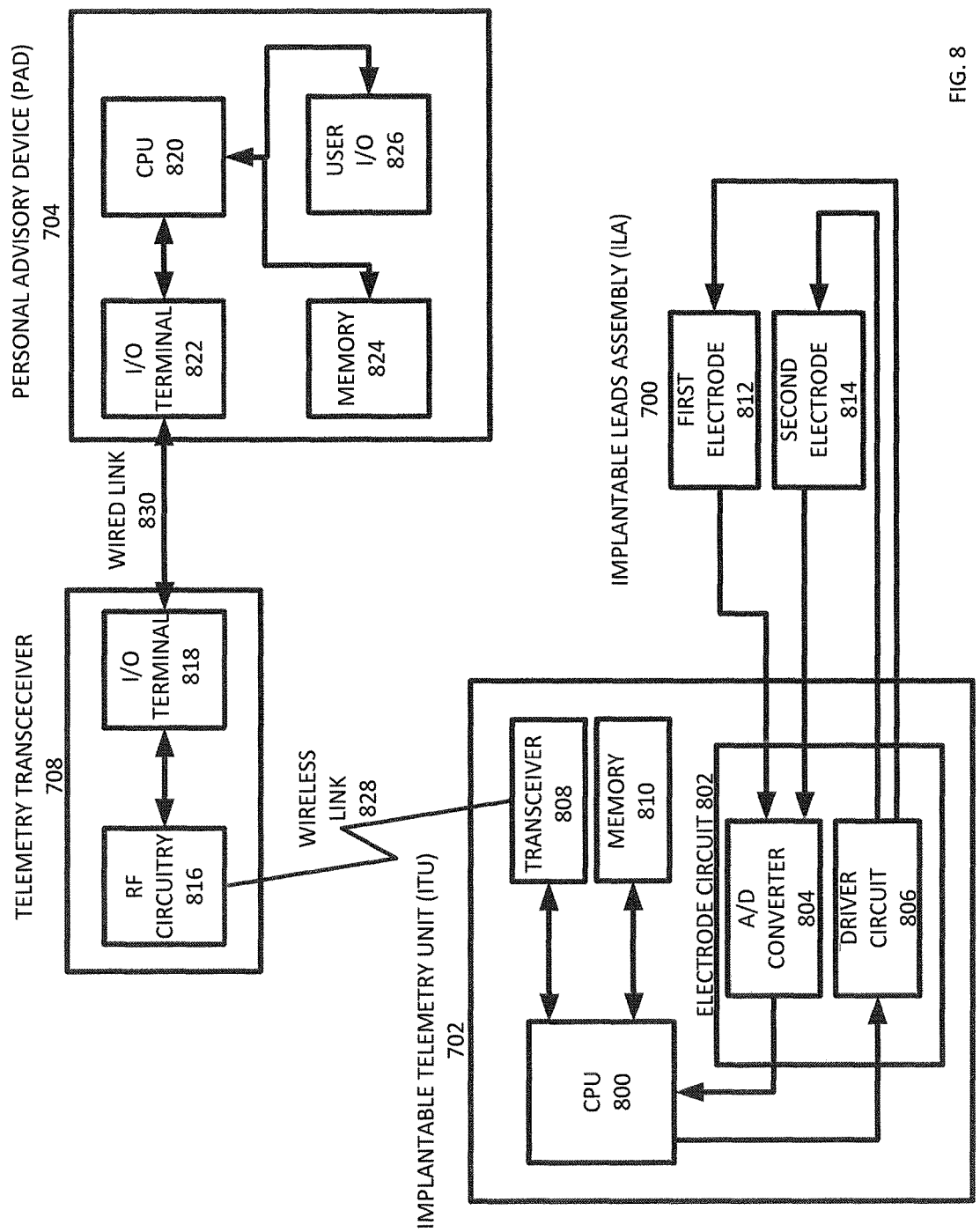
FIG. 8 is a diagram of hardware components of the implantable SAS device, according to an example embodiment.

FIG. 8 shows a block diagram of various hardware components present in the ILA, ITU, PAD and telemetry transceiver shown in FIG. 7. For example, ITU 702 implanted in the dog may include CPU 800, electrode circuit 802 that includes both analog to digital (A/D) converter 804 and driver circuit 806, transceiver 808 and memory 810. The electrode circuit 802 of the ITU is connected via electrical leads to electrodes 812 and 814 of ILA 700 which is also implanted in the dog.

The devices included in the harness of the dog include telemetry transceiver 708 and PAD 704. Telemetry transceiver 708 includes radio frequency (RF) circuitry 816 and input/output (I/O) terminal 818. PAD 704 includes CPU 820, I/O terminal 822, memory 824 and user I/O 826.

During operation, for example, iEEG signals are captured by first electrode 812 and second electrode 814. These iEEG signals are then converted into digital data by A/D converter 804 and then passed to CPU 800 for processing. CPU 800 may perform processing (e.g. filtering) on the iEEG data which is then transmitted wirelessly by transceiver 808 to telemetry transceiver 708 via wireless link 828. RF circuitry 816 processes the wireless data and outputs the data via I/O terminal 818 and wired link 830 to PAD 704.

I/O terminal 822 then inputs the data to CPU 820 which performs processing to predict possible seizures. This algorithm is stored in memory 824 and is described in detail in FIG. 9. Specifically, in step 900 (training phase) CPU 820 receives the iEEG data. In step 904 (training phase), CPU 820 uses Bayesian nonparametric Markov switching process to parse the iEEG data into distinct dynamic event states. In step 906 (training phase), CPU 820 models each event state as a multidimensional Gaussian distribution.

Then, in step 908 (real-time analysis phase), CPU 820 processes the collected data according to the multidimensional Gaussian distributions to determine a probability that the event state is a pre-seizure state in an attempt to identify states that predict future seizures. If CPU 820 predicts a seizure, then in step 910 (therapy phase), CPU 820 provides therapy through electrical stimulation to the brain based on the prediction. Specifically, CPU 820 of PAD 704 instructs (via I/O terminal 822, wired link 830, I/O terminal 818, RF circuitry 816, wireless link 828 and transceiver 808) CPU 800 of ITU 702 to apply an electrical stimulation signal to the dog's brain. In response to this instruction, CPU 800 instructs driver circuit 806 (which may include an electrical signal generator) to apply electrical signals of a certain amplitude, frequency and duration to a specific location of the dog's brain via the first electrode 812 and the second electrode 814 of ILA 700. It is noted that the amplitude, frequency and location of these electrical signals may be generated on a per-patient basis.

Figure 9:
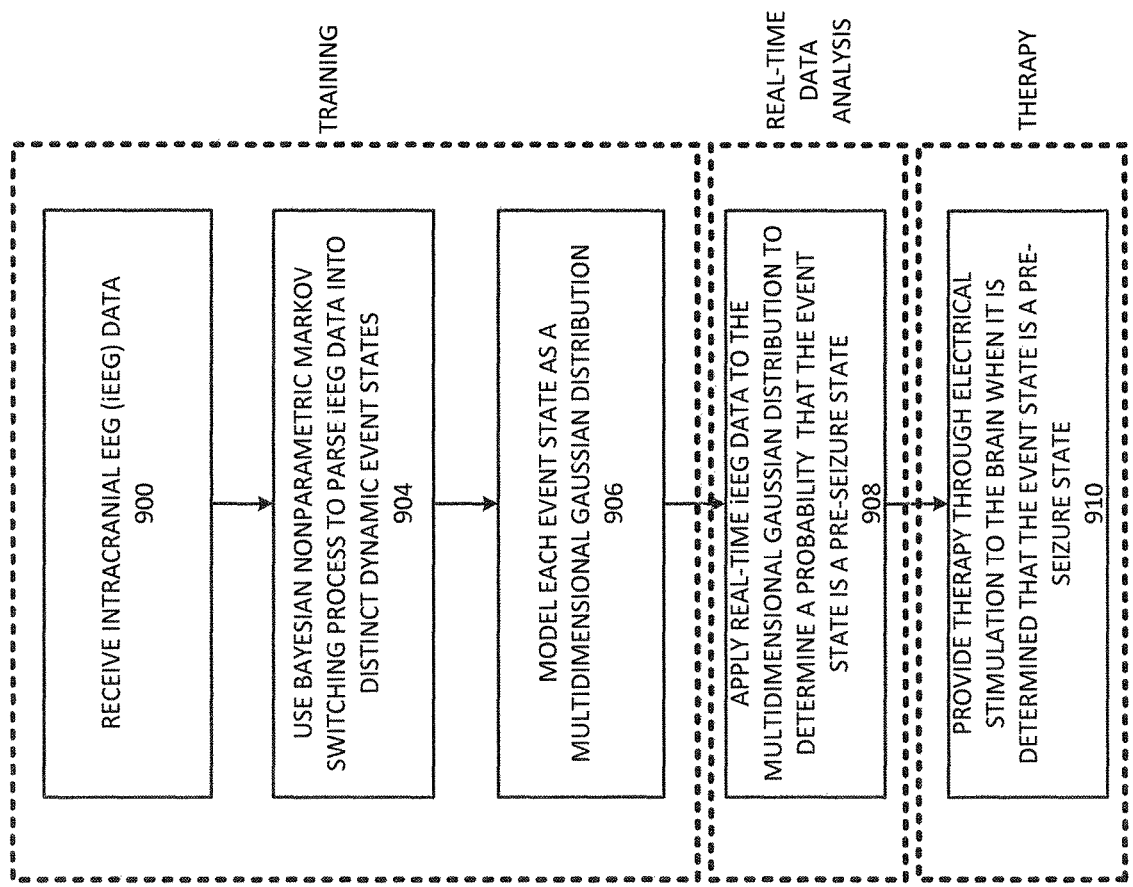
FIG. 9 is a flowchart describing the algorithm for predicting and treating seizures, according to an example embodiment.

In an alternative embodiment, processor 800 of ITU 702 may perform processing steps in FIG. 9 to predict and treat possible seizures without relying on PAD 704. In this embodiment, PAD 704 could simply be used as an alert device to alert a medical technician and/or the patient of predicted seizure activity.

In this example, user I/O 826 of PAD 704 may include outputs such as lights, a speaker, a liquid crystal display (LCD) screen for providing information such as warnings of pending seizures to the user of the PAD. User I/O 826 may also include input devices such as a touch screen and/or a keypad that allows the user of the PAD to provide manual instructions to the PAD.

It should be noted that each of the devices (i.e. ITU, telemetry transceiver and PAD) shown in FIG. 8 are battery powered (not shown). The batteries in each device may be of the chargeable variety. For example, each external device may be charged by plugging the device into an outlet. The implantable device may wirelessly chargeable through inductive power transfer.

In this work, a novel algorithm for individualized seizure prediction suitable for use in a closed loop, implantable system is presented. It is demonstrated that modeling seizure activity using an autoregressive hidden Markov model may provide insights into novel methods of characterizing and analyzing iEEG data. This algorithm represents a substantial improvement in accuracy of seizure prediction over the industry standard, achieving a nearly 98% reduction in false positive rate while slightly improving prediction sensitivity. This work also demonstrates potential for a new pipeline for individualized device data collection, training, and reprogramming utilizing a central cloud-based platform.

Although the system is illustrated and described herein with reference to specific embodiments, it is not intended to be limited to the details shown. Rather, various modifications may be made in the details within the scope and range of equivalents of the claims.

What is claimed:

1. An implantable medical device for predicting and treating electrical disturbances in tissue, the medical device including:
    an implantable telemetry unit (ITU) including a processor and an electrode circuit; and
    an implantable leads assembly (ILA) including a first electrode and a second electrode implantable in the tissue and electrically coupled to the electrode circuit of the ITU,
    wherein the processor of the ITU is configured to perform training by:
        receiving electrical signals input to the electrode circuit by the first and second electrodes,
        parsing the electrical signals into dynamic event states using Bayesian Non-Parametric Markov Switching, and
        modeling each event state as a multi-dimensional probability distribution,
    wherein the processor of the ITU is further configured to perform analysis of the electrical signals and therapy to the tissue by:
        receiving other electrical signals input to the electrode circuit by the first and second electrodes,
        applying the other electrical signals to the multi-dimensional distribution to predict future electrical disturbances in the tissue, and
        controlling the electrode circuit to apply an electrical therapy signal to the first and second electrodes to mitigate effects of the future electrical disturbances in the tissue.

2. The implantable medical device of claim 1, further including:
    a transceiver coupled to the processor,
    wherein the processor is further configured to control the transceiver to wirelessly transmit an alert to a personal advisory device (PAD) when a pre-seizure state is predicted.

3. The implantable medical device of claim 1,
    wherein the electrical signals are intracranial electroencephalogram (iEEG) signals, the tissue is a brain, and the electrical disturbances are seizures.

4. The implantable medical device of claim 3,
    wherein the processor is further configured to:
        identify potential states of interest (SOI) by investigating which event states are enriched in pre-seizure zones during a predetermined time window prior to the onset of the future seizure.

5. The implantable medical device of claim 1,
    wherein the processor is further configured to:
        accumulate time points associated with each event state into separate data sets to provide a matrix for each event state of size N (N being a number of channels produced by the first and second electrodes) by M (M being a number of time points associated with the state).

6. The implantable medical device of claim 1,
    wherein the processor is further configured to:
        utilize the multi-dimensional probability distribution to determine to which state a received signal would most likely belong using a maximum likelihood estimation.

7. The implantable medical device of claim 3,
wherein the processor is further configured to:
- identify pre-seizure states based on a sliding window of incoming data from the first and second electrodes, and
- determine that a pre-seizure state is present when a percentage of points enriched with pre-seizure zones within the sliding window are greater than a threshold percentage.

8. An method for predicting electrical disturbances in tissue using an implantable telemetry unit (ITU) including a processor and an electrode circuit, and an implantable leads assembly (ILA) including a first electrode and a second electrode implanted implantable in the tissue and electrically coupled to the electrode circuit of the ITU, the method including:
- performing training by the processor by:
  - receiving electrical signals input to the electrode circuit by the first and second electrodes;
  - parsing the electrical signals into dynamic event states using Bayesian Non-Parametric Markov Switching;
  - modeling each event state as a multi-dimensional probability distribution;
- performing analysis and therapy by the processor by:
  - receiving other electrical signals input to the electrode circuit by the first and second electrodes,
  - applying the other electrical signals to each multi-dimensional distribution to predict future electrical disturbances in the tissue; and
  - controlling the electrode circuit to apply an electrical therapy signal to the first and second electrodes to mitigate effects of the future electrical disturbances in the tissue.

9. The method of claim 8, further including:
controlling, by the processor, a transceiver to wirelessly transmit an alert to a personal advisory device (PAD) when a pre-seizure state is predicted.

10. The method of claim 8,
wherein electrical signals are intracranial electroencephalogram (iEEG) signals, the tissue is a brain, and the electrical disturbances are seizures.

11. The method of claim 10,
identifying, by the processor, potential states of interest (SOI) by investigating which event states are enriched in pre-seizure zones during a time window prior to the onset of the future seizure.

12. The method of claim 8,
accumulating, by the processor, time points associated with each event state into separate data sets to provide a matrix for each event state of size N (N being a number of channels produced by the first and second electrodes) by M (M being a number of time points associated with the state).

13. The method of claim 8,
utilizing, by the processor, the multi-dimensional probability distribution to determine which state a received signal would most likely belong using a maximum likelihood estimation.

14. The method of claim 10,
identifying, by the processor, pre-seizure states based on a sliding window of incoming data from the first and second electrodes; and
determining, by the processor, that a pre-seizure state is present when a percentage of points enriched with pre-seizure zones within the sliding window are greater than a threshold percentage.

* * * * *

UNITED STATES PATENT AND TRADEMARK OFFICE
CERTIFICATE OF CORRECTION

PATENT NO. : 10,245,431 B2
APPLICATION NO. : 15/333360
DATED : April 2, 2019
INVENTOR(S) : Steven N. Baldassano et al.

Page 1 of 1

It is certified that error appears in the above-identified patent and that said Letters Patent is hereby corrected as shown below:

In the Specification

<u>Column 1</u>
Lines 16-21, delete "This invention was made with government support under grant/contract numbers P20 NS080181 and U01-NS-073557-01A1 awarded by National Institutes of Health and FA9550-12-1-0406; FA9550-12-1-0453 awarded by the Air Force Office of Scientific Research. The government has certain rights in the invention."

And insert:
--This invention was made with government support under Grant Numbers NS080181 and NS073557 awarded by the National Institutes of Health and FA9550-12-10406 and FA9550-12-1-0453 awarded by the United States Air Force. The government has certain rights in the invention.--

Signed and Sealed this
Twenty-third Day of July, 2019

Andrei Iancu
*Director of the United States Patent and Trademark Office*